US005739278A

United States Patent [19]
Daum et al.

[11] Patent Number: 5,739,278
[45] Date of Patent: Apr. 14, 1998

[54] COMPOSITIONS FOR PROTEIN TYROSINE PHOSPHATASES

[75] Inventors: Günter Daum; Deborah E. Cool; Edmond H. Fischer, all of Seattle, Wash.

[73] Assignee: University of Washington, Seattle, Wash.

[21] Appl. No.: 416,035

[22] Filed: Mar. 30, 1995

Related U.S. Application Data

[63] Continuation of Ser. No. 59,949, May 10, 1993, abandoned.
[51] Int. Cl.⁶ .......................... A61K 38/00; A61K 38/02; C07K 5/00; C07K 7/00
[52] U.S. Cl. ..................... 530/328; 530/345; 514/15
[58] Field of Search ..................... 530/327, 328, 530/345; 514/7, 14, 15

*Primary Examiner*—Avis M. Davenport
*Attorney, Agent, or Firm*—Seed and Berry LLP

[57] ABSTRACT

Methods and compositions useful for protein tyrosine phosphatases (PTPs) are disclosed. Peptides are provided which, in one aspect, are useful as substrates for the determination of PTP activity. In contrast to the current approaches, such peptides provide a general substrate for which variations in PTP enzymatic activity due to the assay are minimized. The present invention also discloses methods for determining the presence or amount of PTP. Because of the increased sensitivity of the methods, PTPs can be detected in situations where only limiting amounts of sample, e.g., tissue extracts or immunoprecipitates, are available.

2 Claims, 2 Drawing Sheets

COMPOSITIONS FOR PROTEIN TYROSINE PHOSPHATASES

CROSS-REFERENCE TO RELATED APPLICATION

This application is a continuation of U.S. patent application Ser. No. 08/059,949, filed May 10, 1993, and now abandoned.

TECHNICAL FIELD

The present invention relates generally to methods and compositions useful for protein tyrosine phosphatases. This invention is more particularly related to peptides which have a variety of uses, e.g., as substrates for determining protein tyrosine phosphatase activity.

BACKGROUND OF THE INVENTION

Protein tyrosine phosphatases (PTPs) counteract the action of protein tyrosine kinases (PTKs) by specifically dephosphorylating phosphotyrosyl residues. Since tyrosine phosphorylation is involved in cell growth, differentiation and transformation (for reviews see Cohen et al., *J. Biol.* 265: 7709–7712, 1990; Ullrich et al., *Cell* 61: 203–212, 1990), interest in the nature of PTPs has stemmed mainly from their potential anti-tumorigenic action. This family of enzymes comprises the low molecular weight, intracellular and the receptor-linked transmembrane PTPs (for reviews see Fischer et al., *Science* 253: 401–406, 1991; Saito et al, *Cell Growth Differen.* 2: 59–65, 1991). Within the latter, most contain two catalytic domains although the level of activity of the second domain is still a matter of debate (Streuli et al., *Embo J.* 9: 2399–2407, 1990; Pot et al., *J. Biol. Chem.* 266: 19688–19696, 1991; Wang et al., *Embo J.* 10: 3231–3237, 1991). Homology among PTP catalytic domains is around 40% due to several highly conserved motifs.

The most widely used assays for the determination of PTP activity have been based on the release of phosphate from either proteins (Tonks et al., *J. Biol. Chem.* 263: 6722–6730, 1988) or low molecular weight compounds, such as pNPP (Tonks et. al., *J. Biol. Chem.* 263: 6731–6737, 1988) or phosphotyrosine itself (Mustelin et al., *Proc. Natl. Acad. Sci. USA* 86: 6302–6306, 1989; Zhao et al., *Anal. Biochem.* 202: 361–366, 1992). The use of the latter class of substrates, although easily available, has important limitations. The dephosphorylation of pNPP is not catalyzed by PTPs only, but also by serine/threonine phosphatases (for review see Shenolikar et al., *Advances in Second Messenger and Phosphoprotein Research*, Nishizuka et al. (eds.), ed. 24, Raven Press, New York, N.Y., pp. 1–121) and a number of other proteins. The sensitivity of a spectrophotometric assay with phosphotyrosine is at least two orders of magnitude lower than that involving of $^{32}$P-labeled protein substrates (Zhao et al., *Anal. Biochem.* 202: 361–366, 1992).

Two protein substrates have been widely used for PTP activity measurements, namely, tyrosyl phosphorylated RCML (reduced, carboxamidomethylated, and maleylated lysozyme) and MBP (myelin basic protein). With the growing number of characterized PTPs, however, the disadvantages of these substrates have become increasingly obvious. First, assay conditions differ with the nature of the PTP involved. The low molecular weight PTPs exhibit maximum activity towards the protein substrates at neutral pH (Tonks et al., *J. Biol. Chem.* 263: 6731–6737, 1988), whereas the receptor-linked RPTPα displays only 5%–10% of its maximum activity under these conditions (Daum et al., *J. Biol. Chem.* 266: 12211–12215, 1991). Second, aside from the catalytic domain, there are additional sites of interaction between these substrates and the phosphatases. For instance, MBP itself can act as an activator of PTPs (Tonks et al., *J. Biol. Chem.* 263: 6731–6737, 1988; Zander et al., *Biochemistry* 30: 6964–6970, 1991) which may prevent an exact kinetic characterization of the enzymes in its presence. Third, in the presence of RCML, the wild type T-cell enzyme is 30 times less active than when the C-terminal regulatory/localization domain is removed by limited proteolysis (Zander et al., *Biochemistry* 30: 6964–6970, 1991). This could be due to an interference of this segment with the catalytic site that RCML cannot overcome. Fourth, some compounds have the opposite effect on different PTPs. In the presence of MBP, 5 mM EDTA will inhibit the receptor-linked RPTPα (Daum et al., *J. Biol. Chem.* 266: 12211–12215, 1991) but activate the T-cell enzyme (Zander et al., *Biochemistry* 30: 6964–6970, 1991). With RCML as substrate, divalent cations such as $Mn^{2+}$ strongly activate RPTAα (Daum et al., *J Biol. Chem.* 266: 12211–12215, 1991) but inhibit PTP1B (Tonks et al., *J. Biol. Chem.* 263: 6731–6737, 1988) and TC.PTP.

In summary, the determination of PTP activity using the current approaches in the art is greatly affected by a variety of factors, including the type of enzyme involved, the condition of the assay, and the presence of effectors. Thus, there is a need in the art for new compositions and methods that permit the determination of PTP activity using a general substrate of wide applicability for which variations in enzymatic activity due to the assay itself are minimized. The present invention fulfills this need and further provides other related advantages.

SUMMARY OF THE INVENTION

Briefly stated, the present invention provides methods and peptides that have a variety of uses relating to protein tyrosine phosphatases. In one aspect of the present invention, peptides are provided with and without phosphorylation of the tyrosine residue. In one embodiment, a peptide consists essentially of: Asn-Asp-Tyr-Ile-Asn-Ala-Ser-X, wherein X is an uncharged amino acid. In another embodiment, a peptide consists essentially of: Asn-Asp-Tyr-Ile-Asn-Ala-Ser-X, wherein X is an uncharged amino acid and the Tyr residue is phosphorylated. In another embodiment, a peptide consists essentially of: Asn-Asp-Tyr-Ile-Asn-Ala-Ser-Lys. In another embodiment, a peptide consists essentially of: Asn-Asp-Tyr-Ile-Asn-Ala-Ser-Lys, wherein the Tyr residue is phosphorylated. In another embodiment, a peptide consists essentially of: X-Asn-Asp-Tyr-Ile-Asn-Ala-Ser-Lys, wherein X is Glu or Asp. In another embodiment, a peptide consists essentially of: X-Asn-Asp-Tyr-Ile-Asn-Ala-Ser-Lys, wherein X is Glu or Asp and the Tyr residue is phosphorylated.

In another aspect of the present invention, methods are provided for determining the presence or amount of a protein tyrosine phosphatase. In one embodiment, the method comprises the steps of:

(a) incubating a sample suspected of containing a protein tyrosine phosphatase with a phosphopeptide as set forth above under conditions and for a time sufficient to permit dephosphorylation of the phosphopeptide by a protein tyrosine phosphatase in the sample, wherein the phosphorus atom of the phosphopeptide is radioactive;

(b) separating non-dephosphorylated phosphopeptide from free radioactive phosphorus released by dephosphorylation of the phosphopeptide; and (c) detecting the presence or amount of radioactivity released by dephosphorylation of the phosphopeptide, and therefrom determining the presence or amount of protein tyrosine phosphatase enzymatic activity in the sample.

Other aspects of the invention will become evident upon reference to the following detailed description and attached drawings.

DETAILED DESCRIPTION OF THE INVENTION

Figure 1:
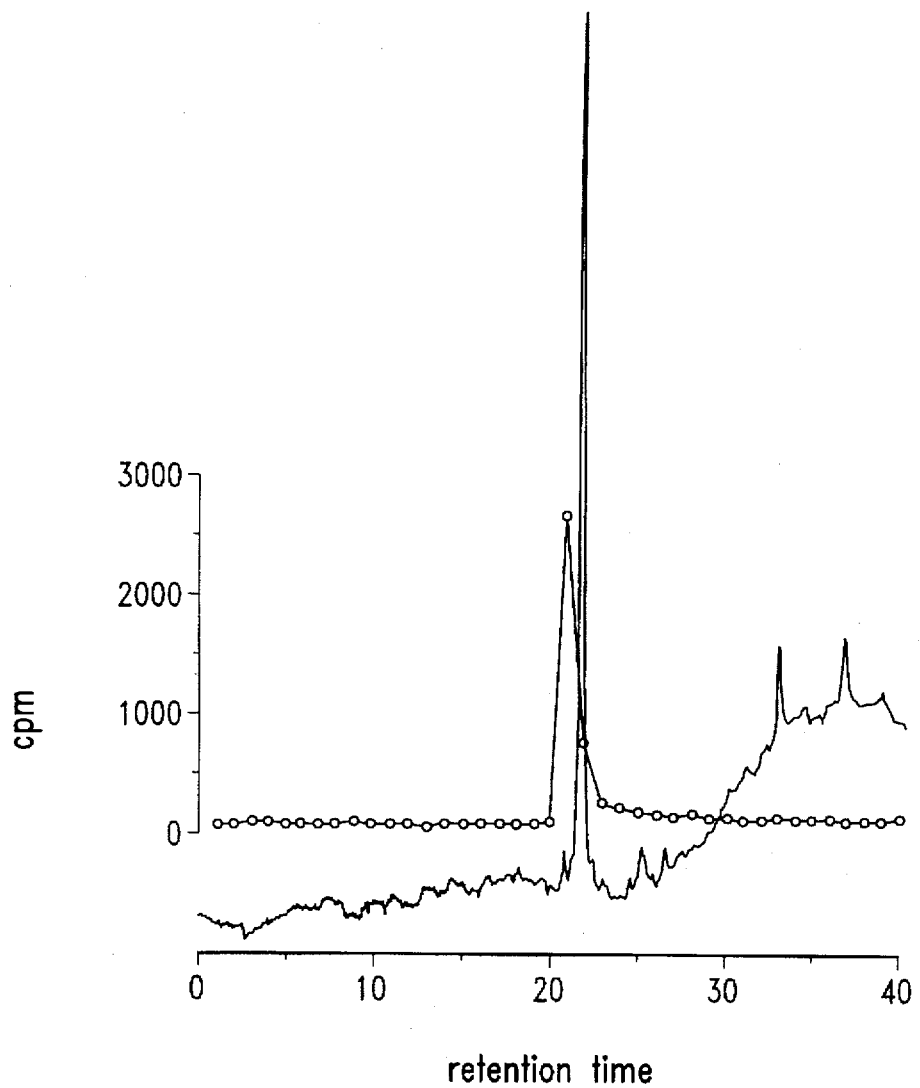
FIG. 1 graphically depicts an HPLC elution profile of the peptide ENDYINASL and its tyrosine phosphorylated form. The non-radioactive peptide (4 µg dissolved in 4 µl of 0.1% trifluoroacetic acid) and an aliquot of freshly phosphorylated tracer were mixed and separated on an ultrosphere C18 column using a Beckmann instrument and a linear gradient from 0%–100% acetonitrile in 0.1% trifluoroacetic acid. The flow rate was 1.0 ml/min. The eluate was monitored at 220 nm for the non-radioactive peptide (full line) and the radioactivity of each fraction was determined for the phosphorylated peptide (open circles).

As noted above, the present invention is directed toward compositions and methods useful for protein tyrosine phosphatases (hereinafter referred to as "PTPs"). One use of the peptide compositions of the present invention is for the determination of PTP activity. As disclosed within the present invention, peptides containing a tyrosine may be phosphorylated and serve as a general substrate of wide applicability to PTPs.

The use of a peptide of the present invention as a substrate for PTP to detect PTP activity is not subject to the limitations of the substrates in the art described above. As shown in the subject disclosure, the assay of the present invention is highly sensitive; all PTPs display near optimum activities under the same assay conditions; and effectors have similar effects on PTPs. This assay permits the detection and characterization of a wide variety of intracellular and receptor-linked PTPs. Further, because of the assay's increased sensitivity, PTPs can be detected in situations where only limiting amounts of sample, e.g., tissue extracts or immunoprecipitates, are available.

In the assay, a sample suspected of containing a PTP is contacted with a phosphorylated peptide of the present invention under conditions and for a time sufficient to permit dephosphorylation. Because of the relatively short half-lives of radioactive forms of phosphorus, peptides of the present invention are generally prepared and stored in non-phosphorylated form. Uses of such peptides include as precursors for the phosphorylated peptides used as substrates for PTPs. Peptides of the present invention are readily prepared using techniques well known to those of ordinary skill in the art. For example, peptides may be synthesized using an instrument, such as those available from Applied Biosystems Inc. (Foster City, Calif.).

In one embodiment, a peptide of the present invention consists essentially of: Asn-Asp-Tyr-Ile-Asn-Ala-Ser-X, wherein X is an uncharged amino acid. Examples of uncharged amino acids include isoleucine, alanine, threonine, proline, etc. It will be evident to those of ordinary skill in the art, when in possession of the present disclosure, that modifications (e.g., additions, deletions and substitutions) may be made to a particular peptide without substantially affecting the peptide's ability to act as a substrate for a PTP. For example, in a preferred embodiment, a glutamic acid residue (Glu) is added to the amino terminus, e.g., to an amino terminal Asn. In a particularly preferred embodiment, a peptide has the sequence: Glu-Asn-Asp-Tyr-Ile-Asn-Ala-Ser-Leu. In another embodiment, a peptide of the present invention consists essentially of: Asn-Asp-Tyr-Ile-Asn-Ala-Ser-Lys. In preferred embodiments, one or two additional lysine residues (Lys) are added to a carboxyl terminal Lys, with or without the addition of a Glu residue at the amino terminus. Such a peptide permits binding to oppositely charged solid supports, such as phosphocellulose paper. In a particularly preferred embodiment, a peptide has the sequence: Glu-Asn-Asp-Tyr-Ile-Asn-Ala-Ser-Lys-Lys-Lys. Other peptides with one or more additions, deletions or substitutions to the sequences described above may be readily tested using the assay protocols provided herein and compared to the results disclosed herein for certain preferred peptides. Based upon the results of tests of any other modified peptides, it will be readily apparent whether a particular peptide is suitable as a PTP substrate. Those of ordinary skill in the art will further appreciate that additions or substitutions of one or more residues in a peptide may be performed using molecules that are not amino acids, but which do not substantially affect a peptide's ability to function as a PTP substrate.

For use in an assay for PTP activity, a peptide of the present invention is phosphorylated on its tyrosine residue. Typically, the radioactive isotope is phosphorus-32. In general, phosphorylation may be accomplished in a variety of ways. Typically, a protein tyrosine kinase is used. For example, a soluble EGF-receptor kinase in combination with $^{32}$P-labeled ATP may be used to phosphorylate a tyrosine residue on a peptide of the present invention. Such a phosphorylation reaction is typically allowed to proceed for about 2 hours at 30° C. or overnight at room temperature. Phosphorylated peptide is then purified from a phosphorylation reaction mixture. For example, peptide may be separated from a reaction mixture by addition of trichloroacetic acid and centrifugation, whereby the peptide remains in the supernate. The peptide is generally further purified by column chromatography, e.g., on C18. Purified phosphorylated peptide may be lyophilized and stored at −20° C. prior to use.

A variety of sources and sample preparations may be analyzed for PTP activity using the assays of the present invention. For example, tissue extracts may be used. In a preferred embodiment, an immunoprecipitate is assayed for PTP activity. The availability of a procedure, as provided herein, for the determination of PTP activity in immunoprecipitates permits the rapid identification of different PTP enzymes in cell extracts without further fractionation or purification. For example, a sample suspected of containing a PTP is incubated with anti-PTP antisera, and protein A attached to a solid support, such as beads, under conditions and for a time sufficient for immunocomplexes to form between PTP and anti-PTP, and for the immunocomplexes to bind to the protein A via the anti-PTP. Typically, the incubation is allowed to proceed overnight at 4° C. with mixing. Following incubation, the protein A beads are washed and tested for PTP activity using a phosphorylated peptide of the present invention as substrate. For example, protein A beads suspected of containing PTP following immunoprecipitation of a sample, are incubated with a phosphorylated peptide ("phosphopeptide") under conditions and for a time sufficient to permit dephosphorylation of phosphopeptide by a PTP on the beads. Typically, the beads and phosphopeptide are incubated for about 10 minutes at about 30° C. in a buffer with pH of about 6.

Following incubation, phosphopeptide which is not dephosphorylated ("non-dephosphorylated phosphopeptide") is separated from radioactivity released by dephosphorylation of phosphopeptide (i.e., from free radioactive phosphorus released by dephosphorylation). As used herein, the term "radioactive phosphorous" includes all forms in which a radioactive phosphorus atom may be present on a tyrosine residue and removed by dephosphorylation, e.g., as a phosphate group. Typically, separation of non-dephosphorylated phosphopeptide from free radioactive phosphorus released by dephosphorylation of phosphopeptide is effected by centrifugation, following termination of the dephosphorylation reaction by the addition of substances including nonradioactive phosphates and charcoal. Radioactivity in the supernate is determined by means well known to those of ordinary skill in the art. Based upon the amount of radioactivity added to the assay initially via the phosphopeptide and the amount of radioactivity detected at the end of the assay as radioactivity released by dephosphorylation, the PTP enzymatic activity of the sample assayed may be calculated. Alternatively, the detection of the presence of a PTP may be sufficient, without quantifying the level of PTP activity.

As noted above, tyrosine phosphorylation is involved in cell growth, differentiation and transformation. Since PTPs have the ability to dephosphorylate a phosphorylated tyrosine, PTPs are important as a family because of their potential in the development of therapeutics, e.g., for cancer, diabetes, auto-immune disorders, multiple sclerosis and muscular dystrophy. The assays of the present invention permit the detection and/or screening of new PTPs, including synthetic and/or truncated forms with therapeutic utility. Further, the present assays may be used to detect and/or screen for PTP inhibitors, whether naturally derived or synthetically produced.

In addition, the peptides of the present invention may be used for purposes other than as substrates (or substrate precursors) for PTPs. For example, certain types of signal transductions may be inhibited by use of a phosphorylated peptide of the present invention. More specifically, the binding of substances (such as growth factors) to certain receptors causes autophosphorylation on tyrosine residues. Proteins then bind to the site of autophosphorylation. By flooding with a phosphorylated peptide, the protein which bind to the site of phosphorylation in signal transduction will be "fooled" into binding to the added phosphorylated peptide. Therefore, such signal transduction is inhibited, which is desirable where phosphorylation in signal transduction is associated with a disease.

The following examples are offered by way of illustration and not by way of limitation.

EXAMPLES

Peptides were synthesized on an Applied Biosystems 430A synthesizer (Foster City, Calif.) and analyzed either at the Howard Hughes Medical Institute or at the Molecular Pharmacology Facility, both at the University of Washington (Seattle, Wash.). $\gamma$-$^{32}$P-ATP was obtained from Amersham (Arlington Heights, Ill.) and Sep Pac C 18 cartridges from Walters (Milford, Mass.). Polypep (low viscosity), Protein A coupled to Sepharose CL-4B, and BSA fraction V were purchased from Sigma (St. Louis, Mo.). Sf9 cells were a gift from Dr. Max Summers, Texas A&M University. The recombinant baculovirus expressing the intracellular kinase domain of the EGF-receptor was a gift from Dr. Joseph Schlessinger, New York University.

The following buffers were used in the examples described below:

(1) Buffer A: 10 mM imidazole-HCl, pH 7.2, 5% glycerol (v/v), 0.1% 2-mercaptoethanol (v/v), 1 µM pepstatin A, 2 µg/ml leupeptin, 20 kallikrein inhibitor units/ml aprotinin;

(2) Buffer B: same as buffer A but with 100 mM imidazole HCl;

(3) Buffer AT: buffer A containing 0.1% Triton X-100;

(4) Buffer E: buffer A containing 2 mM EDTA and 1 mM benzamidine;

(5) Buffer M6: same as buffer AT except that imidazole HCl was replaced by 60 mM MES-NaOH, pH 6.0; and (6) HNTG: 20 mM HEPES, pH 7.5, 150 mM NaCl, 0.1% Triton X-100, 10% glycerol (v/v).

EXAMPLE 1

PHOSPHORYLATION AND PURIFICATION OF PEPTIDES

A. Phosphorylation

The intracellular kinase domain of the EGF-receptor was partially purified from Sf9 cells following infection with a recombinant baculovirus (Hsu et al., *Cell Growth Differ.* 1: 191–200, 1990). After 72–84 hours, cells from 20 175 cm$^2$ flasks were harvested and extracted in 40 ml buffer E by 20 strokes in a Dounce homogenizer. The homogenate was centrifuged for 30 minutes at 100,000 x g. The kinase was extracted from the pellet in 10 ml buffer E containing 0.6M KCl. This extract was cleared by centrifugation as described above and glycerol was added to a final concentration of 20% (v/v). Aliquots of 1 ml were stored at −70° C.

Phosphorylation of peptides was performed in Buffer B containing 0.1 mM peptide, 1 mM $^{32}$P-labeled ATP (600 cpm/pmol), 10 mM MnCl$_2$ and an amount of soluble EGF-receptor kinase obtained from one 175 cm$^2$ flask per 100 nmoles of peptide. The reaction was allowed to proceed 2 hours at 30° C. or overnight at room temperature.

B. Purification Following Phosphorylation

The peptide in the reaction mixture described above in part A was precipitated by adding TCA to a final concentration of 20% (v/v) and separated by 10-minute centrifugation in an Eppendorf centrifuge. The supernatant was passed through a C18 cartridge prewashed with 80% acetonitrile in 1% TFA, then successively with 10 mg/ml Polypep (Sigma), 80% CH$_3$CN in 1% TFA. The peptide was then eluted with 5 ml of 20% CH$_3$CN in 1% TFA, lyophilized and stored at −20° C. Substrate concentrations for phosphatase assays were calculated on the basis of phosphotyrosine content.

C. Calculation of Stoichiometry of Phosphorylation Reaction

The extinction coefficients of the dephosphopeptide and L-tyrosine were found to be identical ($\epsilon_d$=1.42 mM$^{-1}$×cm$^{-1}$ at 274.6 nm). It is assumed that the same is true for the corresponding phosphorylated derivatives, which would result in an $\epsilon_d$ of 0.38 mM$^{-1}$×cm$^{-1}$ at 274.6 nm according to Zhao et al., *Anal. Biochem.* 202: 361–366, 1992. The stoichiometry of the phosphorylation reaction (S) was calculated as follows:

$$S = \frac{c_p}{c_p + c_d} \quad [1]$$

The concentration of the phosphopeptide $c_p$ was assessed by $^{32}P$ measurement. The concentration of the dephospho form $c_d$ according to equation [2], $$c_d = \frac{\frac{A}{d} - \epsilon_p c_p}{\epsilon_d} \quad [2]$$

whereby A=absorption of the substrate mix at 274.6 nm, d=pathlength of cuvette in cm, $\epsilon_d$ and $\epsilon_p$ are the extinction coefficients of the dephospho- and phosphoform of the peptide.

D. Preparation of Phosphorylated ENDYINASL

ENDYINASL was phosphorylated to yield ENDY(P) INASL and purified as described in parts A and B above. Under the conditions described and using the stoichiometry calculations in part C above, the average preparations contained 0.1 mol phosphate/mol peptide. If the reaction was carried out overnight with a second addition of kinase, the stoichiometry of the phosphorylation reaction could reach up to 0.5 mol/mol. A similar high stoichiometry can be obtained by using the insulin receptor as a tyrosine kinase. Analysis of phosphorylated peptide on a C18 HPLC column resulted in a single radioactive peak (FIG. 1). No phosphoserine was detected by phosphoamino acid analysis.

EXAMPLE 2

PHOSPHATASE ASSAYS

A. Protein Tyrosine Phosphatases

The tyrosine phosphatases TC.PTP, TCΔC11.PTP, and RPTPα were purified from infected Sf9 cells as described recently (Zander et al., *Biochemistry* 30: 6964–6970, 1991; Daum et al., *J. Biol. Chem.* 266: 12211–12215, 1991). The 37 kDa form of PTP1B and CD45 were purified from placenta and spleen, respectively (according to Tonks et al., *J. Biol. Chem.* 263: 6722–6730, 1988; Tonks et al., *Biochemistry* 27: 8695–8701, 1988).

B. Immunoprecipitations

Immunoprecipitations were carded out in 500 μl buffer AT containing phosphatase (in the amount indicated in the tables below), 3 μl rabbit antisera #6228 raised against the baculovirus expressed TCΔC11.PTP (Zander et al., *Biochemistry* 30: 6964–6970, 1991) and 20 μl protein A agarose beads. The mixture was rotated overnight at 4° C. The beads were washed three times with HNTG and tested for PTP activity. No PTP activity was detected in controls without antisera.

C. Phosphatase Assays

Phosphatase assays with ENDY(P)INASL were performed in buffer M6. Aliquots of 30 μl or 60 μl containing the phosphopeptide, the phosphatase (-beads) and effectors were incubated for 10 minutes at 30° C. The reaction was stopped by adding 200 μl of a suspension of 10% activated, acid-washed Norit A charcoal (v/v) in 0.9N HCl, 0.1M pyrophosphate and 2 mM NaH$_2$PO$_4$ (according to Streuli et al., *Proc. Natl. Acad. Sci. USA* 86: 8698–8702, 1989). The mixture was cleared by 10-minute centrifugation and the radioactivity of 150 μl of the supernate was determined. Assays with MBP and RCML were performed as described in Tonks et al., *J. Biol. Chem.* 263: 6722–6730, 1988. Protein concentration was determined with BSA as standard (Bradford, *Anal. Biochem.* 72: 248–254, 1976).

The peptide assay was linear up to 40% dephosphorylation with a background of only 0.5%–1% of total radioactivity. All PTPs exhibited an acidic pH optimum with values of 6.5 for PTP1B, 6.0 for TC.PTP, 5.5 for TCΔC11.PTP and CD45, and 5.0 for RPTPα. Therefore, assays were performed at pH 6.0 where every enzyme displayed at least 70% of its maximum activity.

Figure 2A:
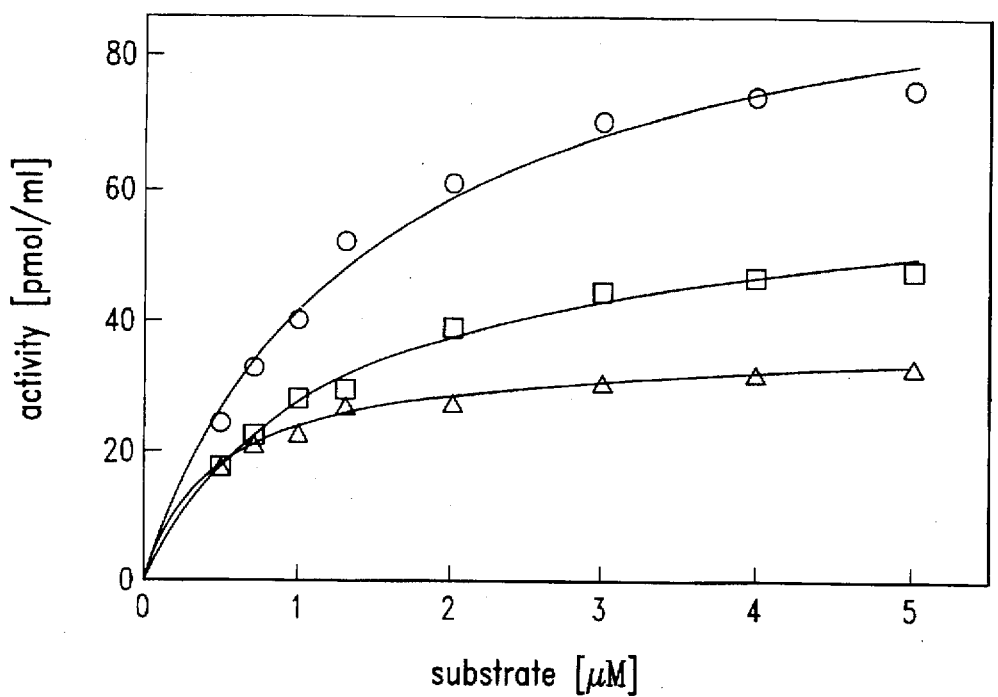
FIGS. 2A–2B graphically illustrates substrate saturation curves of PTPs with ENDY(P)INASL. Assays were performed as described further below. Curve fitting was based on an equation describing a hyperbolic function. Panel A, TCΔC11.PTP (○), TC.PTP (□), and PTP1B (Δ); Panel B, RPTPα (●), CD45 (■).
Figure 2B:
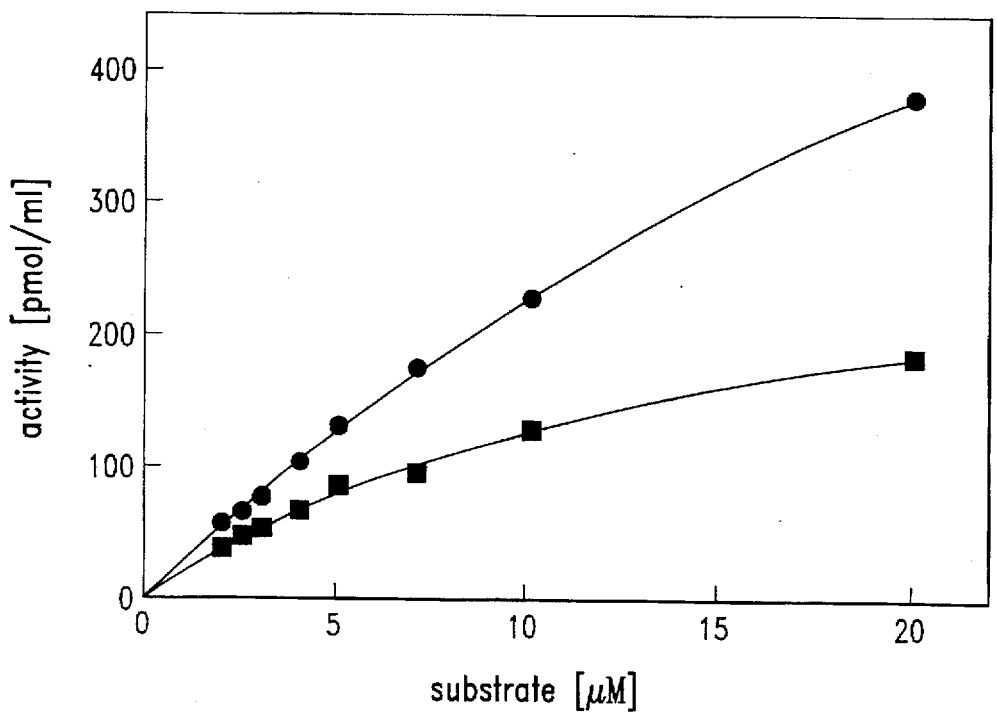

The low molecular weight and the receptor-linked PTPs clearly differed in their kinetic behavior toward ENDY(P) INASL as illustrated in FIGS. 2A and B, respectively. Up to 20 μM phosphopeptide were not sufficient to saturate RPTPα and CD45, whereas TC.PTP, TCΔC11.PTP, and PTP1B exhibited almost maximum activity at 5 μM substrate. Table I summarizes the kinetic constants calculated by non-linear regression analysis of the plots shown in FIG. 2. Besides their higher affinity for the phosphopeptide, both the wild type and truncated forms of the T-cell phosphatase exhibited V$_{max}$ values about ten-fold higher than the receptor-linked enzymes.

TABLE I

KINETIC PARAMETERS USING TYROSYL-PHOSPHORYLATED ENDY(P)INASL AS SUBSTRATE

These were determined by non-linear regression of substrate saturation curves. Mean values of two independent experiments are shown. One unit of activity is defined as the release of 1 nmol phosphate per minute.

| PTP | K$_m$[μM] | V$_{max}$ [U/mg] |
|---|---|---|
| PTP1B | 0.80 +/– 0.45 | —* |
| TCΔC11 | 1.00 +/– 0.40 | 13374 +/– 970 |
| TC20 | 1.13 +/– 0.14 | 14221 +/– 7104 |
| CD45 | 13.84 +/– 0.28 | 1622 +/– 23 |
| RPTPα | 32.49 +/– 3.06 | 1038 +/– 88 |

*No V$_{max}$ value is given because that preparation had been frozen at –70° C. for an extended period of time whereas all other enzymes were from recent preparations.

The properties of PTPs in the presence of effectors are summarized in Table II. Heparin and vanadate strongly inhibited the reaction at concentrations as low as 0.1 μM and 1 μM, respectively. RPTPα was the only enzyme exhibiting some activity (19%) in the presence of 1 μM heparin. All PTPs were also inhibited by divalent cations in the order Zn$^{2+}$>Mn$^{2+}$>Mn$^{2+}$; the low molecular weight PTPs were more affected than the receptor-linked enzymes by low concentrations (e.g., 0.01 mM) of Zn$^{2+}$. There was a slight activation of the low molecular weight enzymes by 1 mM EDTA, but higher concentrations were less effective or even inhibitory. RPTPα and TC.PTP were strongly inhibited by polycations such as spermine and spermidine at concentrations of 1 mM and 5 mM. All other PTPs were only slightly inhibited or unaffected. Interactions between the phosphatases and the dephosphopeptide are very weak since enzyme activities were not or only slightly inhibited by 60 μM ENDYINASL, which corresponds to a substrate/product ratio of 1:60.

TABLE II

Properties of PTPs using ENDY(P)INASL as substrate. Phosphatase activities are given in percent of the value obtained in the absence of effectors.

| effector | concentration | PTP1B | TCΔ-C11 | TC.PTP | CD45 | RPTPα |
|---|---|---|---|---|---|---|
| none | — | 100 | 100 | 100 | 100 | 100 |
| ENDYINASL* | 60 μM | 94 | 71 | 92 | 99 | 76 |
|  | 110 μM | 84 | 55 | 89 | 92 | 54 |
|  | 210 μM | 58 | 46 | 79 | 83 | 30 |
| vanadate | 1.0 μM | 56 | 10 | 32 | 66 | 62 |
|  | 10 μM | 5 | 0 | 3 | 17 | 4 |

TABLE II-continued

Properties of PTPs using ENDY(P)INASL as substrate. Phosphatase activities are given in percent of the value obtained in the absence of effectors.

| effector | concentration | PTP1B | TCA-C11 | TC.PTP | CD45 | RPTPα |
|---|---|---|---|---|---|---|
| | 100 µM | 1 | 0 | 0 | 4 | 0 |
| heparin | 0.01 µM | 91 | 88 | 8 | 8 | 82 |
| | 0.1 µM | 0 | 4 | 1 | 0 | 40 |
| | 1.0 µM | 0 | 0 | 0 | 0 | 19 |
| $Mg^{2+}$ | 1.0 mM | 81 | 75 | 72 | 80 | 90 |
| | 3.0 mM | 73 | 60 | 57 | 62 | 72 |
| | 5.0 mM | 71 | 58 | 60 | 72 | 59 |
| $Mn^{2+}$ | 1.0 mM | 26 | 34 | 49 | 78 | 60 |
| | 3.0 mM | 23 | 22 | 30 | 56 | 38 |
| | 5.0 mM | 20 | 15 | 21 | 44 | 21 |
| $Zn^{2+}$ | 0.01 mM | 65 | 61 | 61 | 92 | 99 |
| | 0.1 mM | 17 | 54 | 26 | 53 | 77 |
| | 1.0 mM | 6 | 21 | 8 | 3 | 4 |
| EDTA | 1.0 mM | 139 | 142 | 119 | 96 | 115 |
| | 3.0 mM | 125 | 109 | 104 | 78 | 97 |
| | 5.0 mM | 110 | 93 | 80 | 76 | 86 |
| spermine | 0.1 mM | 87 | 81 | 119 | 117 | 89 |
| | 0.5 mM | 89 | 60 | 109 | 100 | 57 |
| | 1.0 mM | 82 | 55 | 82 | 85 | 41 |
| spermidine | 0.1 mM | 89 | 67 | 92 | 103 | 72 |
| | 2.0 mM | 94 | 65 | 88 | 92 | 60 |
| | 5.0 mM | 92 | 66 | 91 | 83 | 34 |

*dephosphoform

TC.PTP in quantities between 0.3 and 100 ng were immunoprecipitated. The beads were assayed for PTP activity with ENDY(P)INASL, MBP and RCML as substrates. With the peptide, mounts of the phosphatase as low as 1 ng could be detected, whereas at least 10 ng were required when protein substrates were used (Table III). Furthermore, dephosphorylation of the peptide was proportional to the amount of immunoprecipitated TC.PTP between 1 and 10 ng of the enzyme. In this range, assays of immunoprecipitates could detect 100% of the PTP activity present as compared to assays carried out without previous immunoprecipitation.

TABLE III

Determination of TC.PTP activity in immunoprecipitates PTP activity is expressed as % dephosphorylation, where 100% represents total amount of bound radioactivity in the assay. Assay conditions are described under "Material and Methods."

| TC.PTP ng | Substrates | | |
|---|---|---|---|
| | ENDY(P)INASL | MBP % Dephosphorylation | RCML |
| 0.3 | 0 | 0 | 0 |
| 1 | 1.8 | 0 | 0 |
| 3 | 3.9 | 0 | 0 |
| 10 | 10.8 | 4.1 | 1.4 |
| 30 | 17.5 | 18.6 | 6.1 |
| 100 | 28.1 | 25.5 | 14.3 |

From the foregoing, it will be evident that, although specific embodiments of the invention have been described herein for purposes of illustration, various modifications may be made without deviating from the spirit and scope of the invention.

We claim:

1. A peptide having an amino acid sequence of Glu-Asn-Asp-Tyr-Ile-Asn-Ala-Ser-Leu (Seq. ID No. 6).

2. A peptide having an amino acid sequence of Glu-Asn-Asp-Tyr-Ile-Asn-Ala-Ser-Leu, wherein the Tyr residue is phosphorylated (Seq. ID No. 7).

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /note= "Wherein X is an uncharged amino acid."

( x i ) SEQUENCE DESCRIPTION: SEQ ID NO:1:

Asn Asp Tyr Ile Asn Ala Ser Xaa
    1                      5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 8
    ( D ) OTHER INFORMATION: /note= "Wherein X is an
        uncharged
        amino acid."

( i x ) FEATURE:
    ( A ) NAME/KEY: Modified-site
    ( B ) LOCATION: 3
    ( D ) OTHER INFORMATION: /note= "Wherein Tyr is
        phosphorylated."

( x i ) SEQUENCE DESCRIPTION: SEQ ID NO:2:

Asn  Asp  Tyr  Ile  Asn  Ala  Ser  Xaa
1                       5

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "Wherein Tyr is
            phosphorylated."

( x i ) SEQUENCE DESCRIPTION: SEQ ID NO:3:

Asn  Asp  Tyr  Ile  Asn  Ala  Ser  Lys
1                       5

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Wherein X is Glu or
            Asp."

( x i ) SEQUENCE DESCRIPTION: SEQ ID NO:4:

Xaa  Asn  Asp  Tyr  Ile  Asn  Ala  Ser  Lys
1                       5

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Wherein X is Glu or
            Asp."

( i x ) FEATURE:
        ( A ) NAME/KEY: Modified-site
        ( B ) LOCATION: 4
        ( D ) OTHER INFORMATION: /note= "Wherein Tyr is phosphorylated."

(x i) SEQUENCE DESCRIPTION: SEQ ID NO:5:

Xaa Asn Asp Tyr Ile Asn Ala Ser Lys
1               5

(2) INFORMATION FOR SEQ ID NO:6:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (x i) SEQUENCE DESCRIPTION: SEQ ID NO:6:

Glu Asn Asp Tyr Ile Asn Ala Ser Leu
1               5

(2) INFORMATION FOR SEQ ID NO:7:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 4
    (D) OTHER INFORMATION: /note= "Wherein Tyr is
        phosphorylated."

(x i) SEQUENCE DESCRIPTION: SEQ ID NO:7:

Glu Asn Asp Tyr Ile Asn Ala Ser Leu
1               5

(2) INFORMATION FOR SEQ ID NO:8:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (x i) SEQUENCE DESCRIPTION: SEQ ID NO:8:

Glu Asn Asp Tyr Ile Asn Ala Ser Lys Lys Lys
1               5                   10

(2) INFORMATION FOR SEQ ID NO:9:

(i) SEQUENCE CHARACTERISTICS:
    (A) LENGTH: 8 amino acids
    (B) TYPE: amino acid
    (D) TOPOLOGY: linear (ii) MOLECULE TYPE: peptide (x i) SEQUENCE DESCRIPTION: SEQ ID NO:9:

Asn Asp Tyr Ile Asn Ala Ser Lys
1           5